United States Patent [19]  [11] 4,329,483
Speier  [45] May 11, 1982

[54] PREPARATION OF CYCLOTETRASILOXANES ALIPHATIC CHLORIDES AND ACYL CHLORIDES

[75] Inventor: John L. Speier, Midland, Mich.

[73] Assignee: Dow Corning Corporation, Midland, Mich.

[21] Appl. No.: 282,289

[22] Filed: Jul. 10, 1981

[51] Int. Cl.$^3$ ............................................... C07F 7/08
[52] U.S. Cl. .................................. 556/436; 556/460; 556/452; 556/461; 260/544 Y; 260/544 D; 260/544 L; 260/398; 260/408; 570/181; 570/189; 570/216; 423/325; 423/341
[58] Field of Search ............... 556/460, 436, 452, 461; 260/544 Y, 544 D, 544 L, 398, 408; 423/325, 341; 570/181, 189, 216

[56] References Cited

U.S. PATENT DOCUMENTS

| | | | |
|---|---|---|---|
| 2,891,980 | 6/1959 | Gilbert et al. | 556/460 X |
| 3,803,195 | 4/1974 | Nitzsche et al. | 260/448.2 |
| 4,032,557 | 6/1977 | Spörk et al. | 556/460 X |
| 4,108,882 | 8/1978 | Mahone | 260/448.2 |
| 4,197,251 | 4/1980 | Hirakawa et al. | 556/460 |

*Primary Examiner*—Paul F. Shaver
*Attorney, Agent, or Firm*—George A. Grindahl

[57] ABSTRACT

A method for preparing cyclotetrasiloxane, aliphatic chlorides and/or acyl chlorides from a chlorosilane and an acyloxy compound is disclosed. The chlorosilane and the acyloxy compound may be present as substantially equimolar amounts of separate compounds or they may be present in the same molecule in equimolar amounts. The reactants are merely heated sufficiently, with or without a soluble halide salt catalyst, to form the products. Advantageously this method can provide cyclotetrasiloxanes having water-sensitive radicals such as silicon-bonded chlorine atoms and/or silicon-bonded acyl chloride radicals.

13 Claims, No Drawings

PREPARATION OF CYCLOTETRASILOXANES ALIPHATIC CHLORIDES AND ACYL CHLORIDES

BACKGROUND OF THE INVENTION

The present invention relates to a method for preparing cyclotetrasiloxanes from chlorosilanes without the concomitant preparation of hydrogen chloride or hydrochloric acid. More specifically the present invention relates to a method for preparing cyclotetrasiloxanes from chlorosilanes and an acyloxy compound and coproducing an aliphatic chloride and/or an acyl chloride.

Cyclotetrasiloxanes, particularly cyclotetradiorganosiloxanes such as cyclotetradimethylsiloxanes, are valuable materials because they can be further polymerized to prepare higher molecular weight silicone compositions, such as oils, gums and resins, and because they are useful, without further processing, as fluids.

It is well known that dihydrocarbyldichlorosilanes can be hydrolyzed to prepare poly(dihydrocarbylsiloxanes) and hydrochloric acid. This method, although finding extensive commercial use, has several disadvantages. For example, the by-produced hydrochloric acid is an undesired by-product because it is corrosive, it cannot be used directly to form more dihydrocarbyldichlorosilane and it frequently reacts further with the hydrocarbyl radicals, such as methyl and vinyl radicals. Furthermore, this hydrolysis process does not produce only cyclopolysiloxanes, much less only cyclotetrasiloxanes, but rather a mixture of various linear and cyclic polysiloxanes. Also, this hydrolysis process cannot be used to prepare cyclopolysiloxanes bearing water-sensitive radicals such as silicon-bonded chlorine atoms or acyl chloride radicals.

U.S. Pat. No. 4,108,882 (Mahone) addresses some of the above-noted disadvantages and relates to a process for reacting certain alkyl silanes bearing 1 or 2 silicon-bonded chlorine atoms with methanol in the presence of a quaternary ammonium halide salt catalyst to provide certain alkylpolysiloxanes, including cyclopolysiloxanes, and methyl chloride. As noted in Mahone's patent, this process produces methyl chloride which can be used directly to produce more methylchlorosilanes. However, Mahone's process also produces hydrogen halide, which is undesirable, and, furthermore, the process does not provide cyclopolysiloxanes which bear water-sensitive radicals such as silicon-bonded chlorine atoms or silicon-bonded acyl chloride radicals.

U.S. Pat. No. 3,803,195 (Nitzsche et al.) also addresses some of the above-noted disadvantages and relates to a method for preparing organopolysiloxanes and alkyl halides which comprises passing organohalosilanes and organic compounds of the formula ROR' countercurrently through a reaction zone heated to 20° to 150° C. and containing an essentially inert, acid-resistant packing material of selected surface area. As noted by Nitzsche et al. this method produces alkyl halides which can be used directly to form more alkylhalosilanes. However, Nitzsche et al. discloses that aqueous hydrogen halides are formed as a by-product, in minor amounts, and the packing material must consequently be acid-resistant.

The organic compounds of the formula ROR' that are used in the Nitzsche et al. method encompass alkanols, such as methanol; dialkyl ethers, such as dimethyl ether; alkanoic acid alkyl esters, such as methyl acetate; and mixtures thereof, such as a mixture of methanol and methyl acetate. However, Nitzsche et al. does not teach how to use alkanoic acid alkyl esters in the disclosed process.

Nitzsche et al. further teaches that, although the ratio of organic compound ROR' to organohalosilane is not critical, there should preferably be from 1.0 to 1.75 moles of the ROR' compound for every gram atom of halogen in the organohalosilane when the ROR' compound is an alkanoic acid alkyl ester. Surprisingly, I have found that when said ratio has a value substantially less than 1.0, specifically from 0.25 to 0.5, depending upon the halosilane, there is produced an optimum yield of cyclotetrasiloxane and aliphatic chloride and/or acyl chloride.

Nitzsche et al. teaches that the method disclosed therein produces cyclic and/or linear organopolysiloxanes, however, if exclusively cyclic organopolysiloxanes are desired the coproduced linear organopolysiloxanes must be separated from the cyclic product and recycled through the reaction vessel being used in the method of the invention. Surprisingly, I have found that the method of this invention produces cyclotetrasiloxanes as substantially the only siloxane reaction product.

There is thus provided by this invention a method for producing cyclotetrasiloxanes from chlorosilanes that has many advantages over the processes of the art and avoids many of the disadvantages of the processes of the art.

BRIEF SUMMARY OF THE INVENTION

It is an object of the present invention to provide a method for preparing cyclotetrasiloxanes, as substantially the sole polysiloxane product, from chlorosilanes. It is another object of this invention to provide a method for preparing cyclotetrasiloxanes from chlorosilanes that does not co-produce hydrogen chloride or hydrochloric acid. It is a further object of this invention to provide a method for preparing cyclotetrasiloxanes that bear water-sensitive, silicon-bonded radicals. It is yet another object of this invention to provide a method for preparing cyclotetrasiloxanes from chlorosilanes while coproducing an aliphatic chloride and/or acyl chloride. It is also an object of this invention to provide a process for preparing acyl chlorides and aliphatic chlorides from aliphatic esters of hydrocarbon acids.

These objects, and others which will become obvious to one of ordinary skill in the siloxane synthesis art upon considering the following disclosure and appended claims, are obtained by the method of this invention, which, broadly characterized, comprises heating a reaction mass comprising equimolar amounts of a silane reaction site bearing at least two silicon-bonded chlorine atoms and a hydroxyl-free acyloxy reaction site. Depending on the desired reaction products the silane reaction site and the acyloxy reaction site can be part of the same molecule or of separate molecules. The reaction of this invention can furthermore be facilitated by the use of catalytic amounts of a halide salt catalyst possessing sufficient solubility in the reaction mass during the heating process.

DETAILED DESCRIPTION OF THE INVENTION

The present invention relates to a method for preparing a cyclotetrasiloxane and aliphatic chloride and/or an acyl chloride, said method comprising heating a reaction mass selected from the group consisting of (A) a silylhydrocarbonoxy acylate having the formula $R^1_a Cl_{(3-a)}SiQO_2CR^2$, (B) a hydrocarbonoxy silylacylate having the formula $R^1_a Cl_{(3-a)}SiQCO_2R^2$ and (C) a mixture of equimolar amounts of (i) a silane having the formula $R^1_b SiCl_{(4-b)}$ and (ii) an acyloxy compound selected from the group consisting of hydrocarbon carboxylic esters and hydrocarbon carboxylic anhydrides, wherein, in each occurance, a denotes a number having a value of 0 or 1; b denotes a number having a value of 0, 1 or 2; $R^1$ denotes a monovalent substituted or unsubstituted hydrocarbon radical; $R^2$ denotes a monovalent unsubstituted hydrocarbon radical; Q denotes a divalent substituted or unsubstituted hydrocarbon radical; any hydrocarbon radical bonded to an oxygen atom of an acyloxy radical being bonded at an aliphatic carbon of said any hydrocarbon radical; said heating being sufficient to produce a cyclotetrasiloxane wherein each silicon atom bears two-fewer chlorine atoms than were present on each silicon atom in the reaction mass and at least one reaction product selected from the group consisting of an acyl chloride and an aliphatic chloride; the substituents of said substituted hydrocarbon radicals being non-reactive during said heating.

As noted above, the reaction mass to be heated in the method of this invention consists of equimolar amounts of a silane reaction site and an acyloxy reaction site. By equimolar amounts it is meant molar amounts that provide no more than about a 10 percent molar excess of either reaction site. Thus the molar ratio of silane reaction site to acyloxy reaction site has a value of from about 0.9/1.0 to about 1.1/1.0. The use of less than an equimolar amount of acyloxy reaction site leads to reduced yields of desired reaction products.

The silane reaction site and the acyloxy reaction site can be in the same molecule or in separate molecules, thereby giving rise to two aspects of this invention. In each aspect the reaction products that are produced by the method of this invention comprise a cyclotetrasiloxane and an aliphatic chloride and/or an acyl chloride.

In one aspect of this invention the silane reaction site and the acyloxy reaction site are present in the same molecule to provide a reaction mass consisting essentially of a silylhydrocarbonoxy acylate having the formula (A) or a hydrocarbonoxy silylacylate having the formula (B).

$$R^1_a Cl_{(3-a)}SiQOCR^2 \quad (A)$$
$$\overset{O}{\underset{\|}{}}$$

$$R^1_a Cl_{(3-a)}SiQCOR^2 \quad (B)$$
$$\overset{O}{\underset{\|}{}}$$

When reaction mass (A) is heated sufficiently an aliphatic chloride-substituted cyclotetrasiloxane having the formula

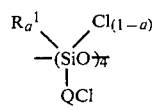
QCl and an acyl chloride having the formula $R^2COCl$ are formed.

When reaction mass (B) is heated sufficiently an acyl chloride-substituted cyclotetrasiloxane having the formula

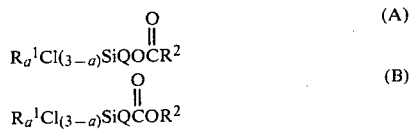
QCOCl and an aliphatic chloride having the formula $R^2Cl$ are obtained.

In formulae (A) and (B) a denotes a number having a value of 0 or 1, thereby requiring 3 or 2, respectively, silicon-bonded chlorine atoms for every silicon atom in the reaction mass. Preferably a has a value of 1 thereby providing, after heating, valuable cyclotetrasiloxanes which are free of silicon-bonded chlorine atoms. Advantageously, when a has a value of 0 cyclotetrasiloxanes bearing silicon-bonded chlorine atoms are obtained which are otherwise difficult to obtain.

In reaction mass (A) and (B) the silane reaction site is bonded to the acyloxy reaction site by way of a divalent hydrocarbon radical Q. This Q radical is bonded by one of its valences to the silicon atom at either an aliphatic or aromatic carbon atom of the Q radical, and by its remaining valence to the acyloxy oxygen atom in (A) at an aliphatic carbon atom of the Q radical or to the acyloxy carbon atom in (B) at either an aliphatic or aromatic carbon atom of the Q radical. This bonding is required because a reaction mass wherein the acyloxy reaction site contains a

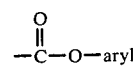

linkage is not sufficiently reactive to produce the desired reaction products.

Unsubstituted divalent hydrocarbon radicals contemplated by Q include aliphatic radicals; such as alkylene radicals having the formula $-C_nH_{2n}-$, wherein n is a positive integer, such as

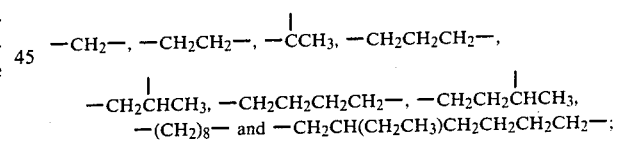

and cycloaliphatic radicals, such as cyclohexylene; and aromatic radicals; such as $-Ay-$, $-AyCH_2-$, $-AyCH_2CH_2-$, $-CH_2AyCH_2-$, $-CH_2CH_2AyCH_2CH_2-$, $-CH_2CH(Ph)CH_2-$ and

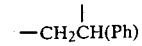

wherein Ay denotes the phenylene radical and Ph denotes the phenyl radical. Said divalent hydrocarbon radicals contemplated for Q can also bear aliphatic unsaturation such as is found in $-CH_2CH=CHCH_2-$, cyclohexenylene and

Preferably Q is an unsubstituted alkylene radical having the formula —$C_nH_{2n}$— wherein n has a value of from 2 to 4, such as —$CH_2CH_2$—, —$CH_2CH_2CH_2$—,

Substituted divalent hydrocarbon radicals contemplated by Q include the unsubstituted divalent hydrocarbon radicals contemplated above wherein one or more hydrogen atoms have been replaced by a substituent which is non-reactive during the heating step in the method of this invention. Examples of said substituents include halogen, preferably chlorine and fluorine, nitro and cyano. Preferably said substituent is separated from the silicon atom by at least 3 carbon atoms.

In reaction mass (A) and (B) $R^1$ denotes a monovalent substituted or unsubstituted hydrocarbon radical and $R^2$ denotes a monovalent unsubstituted hydrocarbon radical. As noted above for any Q radical bonded to an acyloxy oxygen atom, when $R^2$ is bonded to an acyloxy oxygen atom it is bonded thereto at an aliphatic carbon atom of the $R^2$ radical. When $R^2$ is bonded to the acyloxy carbon atom, it can be bonded thereto at an aliphatic or aromatic carbon atom of the $R^2$ radical.

Unsubstituted monovalent hydrocarbon radicals contemplated by $R^1$ and $R^2$ include any hydrocarbon radical having from 1 to 18 carbon atoms, preferably 1 to 6 carbon atoms, such as alkyl radicals, such as methyl, ethyl, propyl, isopropyl, butyl, isobutyl, hexyl, 2-ethylhexyl, octyl, decyl and octadecyl; alkenyl radicals, such as vinyl and allyl; alkynyl radicals; such as propargyl; cycloaliphatic radicals, such as cyclohexyl and cyclohexenyl; aryl radicals, such as phenyl, naphthyl, tolyl, xylyl and xenyl; and aralkyl radicals, such as benzyl, beta-phenylethyl, beta-phenylpropyl and gamma-tolylpropyl. Most preferably $R^1$ is the methyl radical and $R^2$ is a lower alkyl radical, such as methyl, ethyl, propyl, butyl, isopropyl and isobutyl.

Substituted monovalent hydrocarbon radicals contemplated by $R^1$ include the unsubstituted monovalent hydrocarbon radicals contemplated above wherein one or more hydrogen atoms have been replaced by a substituent which is non-reactive during the heating step in the method of this invention. Examples of said substituents include halogen, preferably chlorine and fluorine, nitro and cyano. Preferably said substituent is a halogen atom and is separated from the silicon atom by at least 3 carbon atoms.

Examples of substituted monovalent hydrocarbon radicals contemplated by $R^1$ include —$CH_2CH_2CH_2Cl$, —$CH_2CH_2CF_3$, —AyCl, —$AyNO_2$ and —$CH_2CH(CH_3)CH_2Cl$.

Herein Ay, Ph, $Pr_f$, $Pr_{Cl}$, Vi and $Bu_{Cl}$ denote, respectively, —$C_6H_4$—, $C_6H_5$—, $CF_3CH_2CH_2$—, $ClCH_2CH_2CH_2$—, $CH_2$=CH— and $ClCH_2CH(CH_3)CH_2$—.

Examples of reaction mass (A) which are suitable for use in the method of this invention include, but are not limited to, the following:

$Cl_3SiCH_2CH_2O_2CCH_3$, $Cl_3SiCH_2CH_2$-$H_2O_2CCH_2CH_3$, $CH_3(Cl)_2SiCH_2CH(CH_3)C$-$H_2O_2CCH_3$, $CH_3(Cl)_2SiCH_2CH(CH_3)C$-$H_2O_2CCH_2CH_3$, $CH_3(Cl)_2SiCH_2CH_2C$-$H_2O_2CCH_2CH_3$, $CH_3(Cl)_2SiCH_2CH_2CH_2O_2CCH_3$, $Ph(Cl)_2SiCH_2CH_2CH_2O_2CCH_3$, $Ph(Cl)_2SiCH_2CH(CH_3)CH_2O_2CCH_3$, $Vi(Cl)$-$2SiCH_2CH_2CH_2O_2CCH_3$, $Vi(Cl)_2SiCH_2CH_2C$-$H_2O_2CCH_2CH_3$, $Pr_f(Cl)_2SiCH_2CH_2CH_2O_2CCH_3$, $Pr_f(Cl)_2SiCH_2CH_2CH_2O_2CCH(CH_3)_2$, $Pr_{Cl}(Cl)_2SiCH_2CH_2CH_2O_2CCH_3$, $Pr_{Cl}(Cl)_2SiCH_2CH_2CH_2O_2CCH_2CH_3$, $CH_3(Cl)_2SiCH_2CH_2CH_2O_2CC(CH_3)_3$, $CH_3(Cl)_2SiCH_2CH_2CH_2O_2CCH(CH_3)_2$, $CH_3(Cl)_2SiCH_2CH_2CH_2O_2CPh$, $Bu_{Cl}(Cl)$-$2SiCH_2CH_2CH_2O_2CCH_3$, and $Bu_{Cl}(Cl)_2SiCH_2CH_2C$-$H_2O_2CCH_2CH_3$.

Examples of reaction mass (B) which are suitable for use in the method of this invention include, but are not limited to, the following:

$Cl_3SiCH_2CH_2CH_2CO_2CH_3$, $Cl_3SiCH_2CH(CH_3)CH$-$2CO_2CH_2CH_3$, $Cl_3SiAyCO_2CH_3$, $CH_3(Cl)_2SiCH_2CH(CH_3)CH_2CO_2CH_3$, $CH_3(Cl)_2SiCH_2CH_2CO_2CH_3$, $CH_3(Cl)_2SiCH_2CH(CH_3)CH_2CO_2CH_2CH_3$, $CH_3(Cl)_2SiCH_2CH_2CH_2CO_2CH_2CH_3$, $Ph(Cl)_2SiCH_2CH_2CH_2CO_2CH_3$, $Ph(Cl)_2SiCH_2CH(CH_3)CH_2CO_2CH_3$, $Vi(Cl)$-$2SiCH_2CH_2CH_2CO_2CH_3$, $Vi(Cl)_2SiCH_2CH_2CH$-$2CO_2CH_2CH_3$, $Pr_f(Cl)_2SiCH_2CH_2CH_2CO_2CH_3$, $Pr_f(Cl)_2SiCH_2CH_2CH_2CO_2CH(CH_3)_2$, $Pr_{Cl}(Cl)_2SiCH_2CH_2CH_2CH_2CO_2CH_3$, $Pr_{Cl}(Cl)_2SiCH_2CH_2CH_2CO_2CH_2CH_3$, $CH_3(Cl)_2SiCH_2CH_2CH_2CO_2C(CH_3)_3$, $CH_3(Cl)_2SiCH_2CH_2CO_2CH_3$, $CH_3(Cl)_2SiAyCO_2CH_3$, $CH_3(Cl)_2SiCH_2CH(CH_3)CO_2CH_3$, $Bu_{Cl}(Cl)$-$2SiCH_2CH_2CH_2CO_2CH_3$, $Bu_{Cl}(Cl)_2SiCH_2CH$-$2CO_2CH_2CH_3$ and $Bu_{Cl}(Cl)_2SiCH_2CH(CH_3)CO_2CH_3$.

Reaction mass (A) and (B) can be prepared by any suitable method. Preferably a suitable chlorohydrosilane is added to a suitable aliphatically unsaturated acyloxy compound in a hydroxilylation reaction. Preferably the hydrosilylation reaction is catalyzed by a platinum-containing catalyst.

By way of example, $CH_3(Cl)_2SiH$ can be added to $CH_2$=$C(CH_3)CO_2CH_3$ in a hydrosilylation reaction to provide $CH_3(Cl)_2SiCH_2CH(CH_3)CO_2CH_3$ or to $CH_2$=$CHCH_2O_2CCH_3$ to provide $CH_3(Cl)_2SiCH_2CH_2CH_2O_2CCH_3$. Analogously, other reaction masses (A) and (B) contemplated herein can be synthesized from the appropriate chlorohydrosilane and the appropriate aliphatically unsaturated acyl compound. Hydrosilylation is a well-known synthesis reaction in the organosilicon art and needs no further elaboration herein. Other suitable synthesis methods and schemes will be obvious to one skilled in the organosilicon art.

In another aspect of this invention the silane reaction site and the acyloxy reaction site are present in separate molecules to provide a reaction mass (C) consisting essentially of a mixture of equimolar amounts of a silane (i) having the formula $R^1{}_bSiCl_{(4-b)}$ and an acyloxy compound (ii) selected from the group consisting of hydrocarbon carboxylic esters and hydrocarbon carboxylic anhydrides.

When reaction mass (C) is heated sufficiently a cyclotetrasiloxane having the formula

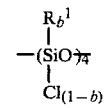

is formed along with an acyl chloride and, additionally when (ii) is a hydrocarbon carboxylic ester, an aliphatic chloride.

In the formula for silane (i) which forms a part of reaction mass (C) b denotes a number having a value of 0, 1 or 2, thereby requiring 4, 3 or 2, respectively, silicon-bonded chlorine atoms for every silicon atom in the reaction mass. Preferably b has a value of 2, thereby providing, after heating, valuable cyclotetradiorganosiloxanes which are free of silicon-bonded chlorine atoms. Advantageously, when b has a value of 0 or 1 cyclotetrasiloxanes bearing silicon-bonded chlorine atoms are obtained which are otherwise difficult to obtain.

In the formula for silane (i) each $R^1$ denotes, independently, any of the substituted and unsubstituted monovalent hydrocarbon radicals contemplated or indicated as being preferred or delineated above for reaction mass (A) and (B). The methyl radical is a preferred unsubstituted $R^1$ radical and halogenated radicals are preferred substituted $R^1$ radicals in silane (i).

Examples of silane (i) which are suitable for use in this second aspect of the method of this invention include, but are not limited to, the following: $SiCl_4$, $CH_3SiCl_3$, $PhSiCl_3$, $Pr_fSiCl_3$, $Pr_{Cl}SiCl_3$, $ViSiCl_3$, $Bu_{Cl}SiCl_3$, $(CH_3)_2SiCl_2$, $CH_3(Vi)SiCl_2$, $CH_3(Ph)SiCl_2$, $CH_3(Pr_f)SiCl_2$, $CH_3(Pr_{Cl})SiCl_2$, $CH_3(Bu_{Cl})SiCl_2$, $(Ph)_2SiCl_2$, $(Ph((Vi)SiCl_2$, $(Ph)(Pr_f)SiCl_2$, $(Ph)(Pr_{Cl})SiCl_2$ and $(Ph)(Bu_{Cl})SiCl_2$.

Many silanes encompassed by (i) are well-known materials whose synthesis needs no further elaboration herein. Suffice it to say that several can be prepared by the direct reaction of a hydrocarbon halide with elemental silicon in the well-known manner. Advantageously the method of this invention can provide desired aliphatic chlorides which can be used in said direct reaction.

Other silanes encompassed by (i) can be prepared by the well-known reaction of an aliphatically unsaturated material; such as an olefin, such as $CH_2=CH_2$, $CH_2=CHCH_3$, $CH_2=CHCF_3$, $CH_2=CHCH_2Cl$ and $CH_2=CH(CH_3)CH_2Cl$ and a suitable chlorohydrosilane; such as $CH_3(Cl)_2SiH$, $Ph(Cl)_2SiH$ and $Cl_2SiH_2$.

Acyloxy compound (ii) which forms a part of reaction mass (C) can be any hydrocarbon carboxylic ester, which contains a

—aliphatic linkage, or any hydrocarbon carboxylic anhydride.

Acyloxy compound (ii) can have an open chain structure or a cyclic structure. Accordingly, acyloxy compound (ii) contemplates esters having the formula

, lactones having the formula

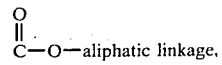

and anhydrides having the formulae

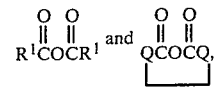

wherein $R^1$ and Q have the meanings denoted above. Preferably acyloxy compound (ii) has the formula

wherein $R^2$ has the meaning denoted above.

Examples of acyloxy compounds (ii) which are suitable for use in this second aspect of the method of this invention include, but are not limited to, the following: $CH_3CO_2CH_3$, $CH_3CO_2CH_2CH_3$, $CH_3CO_2CH(CH_3)_2$, $CH_3CO_2C(CH_3)_3$, $CH_3CH_2CO_2CH_3$, $CH_3CH_2CO_2CH_2CH_3$, $(CH_3)_3CCO_2CH_3$, $PhCO_2CH_3$, $PhCO_2CH_2CH_3$, $CH_2=C(CH_3)CO_2CH_3$,

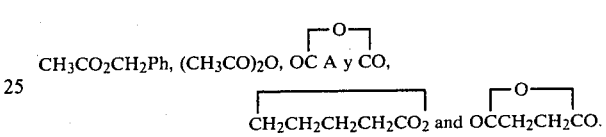

Most preferably acyloxy compound (ii) is an ester having the formula $R^2CO_2R^2$ wherein each $R^2$ denotes, independently, a lower alkyl radical, such as methyl, ethyl, propyl, isopropyl and tertiary butyl.

In the method of this invention the reaction mass is heated sufficiently to provide the desired cyclotetrasiloxane and aliphatic chloride and/or acyl chloride reaction products. By heated sufficiently it is meant the use of any combination of temperature and time that will provide the desired results.

The amount of heating that is sufficient will depend upon the particular reaction mass that is being heated and whether or not said reaction mass further comprises an effective amount of a halide salt catalyst, delineated below. Generally, heating at temperatures greater than 200° C. for a period of time exceeding 15 hours is required to produce significant amounts of desired reaction products when said catalyst is not present. The use of a catalyst permits the use of less-vigorous heating; significant, and sometimes quantitative, yields of desired reaction product being obtained with heating at for example 100° C. for 2 hours, or at 130° C. for 0.3 hours. Sufficient heating can be readily determined by routine experimentation, especially after one considers the numerous examples disclosed herein. An upper temperature limit of about 300° C. seems to be indicated by said examples.

The method of this invention can be performed at any pressure such as at subatmospheric, atmospheric or superatmospheric pressure and in either a closed or open system. Preferably the more-volatile reaction masses are heated in a pressure system and the less-volatile reaction masses are heated in a vented system. The particular method of heating the reaction mass is not critical and one of ordinary engineering skill will be able to devise a particular system to achieve typical production goals such as continuous or batch processing, continuous removal of a particular reaction product from the reaction zone, recycling of unspent reactants and catalyst and the like.

The process of this invention is facilitated by the use of a catalytic amount of a halide salt. For example, in some instances the use of a catalyst provides a quantitative yield of reactive product in 4 hours whereas the same reaction mass containing no catalyst produces substantially no product in 72 hours at substantially the same temperature. In other instances the use of a catalyst provides a quantitative yield of reaction product at a substantially lower temperature and shorter time span for a reaction mass that otherwise provides only minimal amount of reaction product.

Any halide salt which has appreciable solubility in the reaction mass during the heating thereof is effective in the method of this invention. Iodide salts are more effective than bromide salts which are more effective than chloride salts. Quaternary ammonium, pyridinum and phosphonium halides are preferred halide salts because of their appreciable solubility in the reaction mass. Metal halides, such as $AlCl_3$ and $ZnCl_2$, having appreciable solubility in the heated reaction mass are also effective catalysts in the method of this invention.

While not limiting this invention by theory, I believe that the reaction of this invention proceeds by way of nucleophilic attack of a carbonyl group of the acyloxy reaction site on the chlorosilane reaction site and this attack is facilitated by complexation of the halide salt with the acyloxy carbonyl group. Accordingly, any halide salt having some solubility in the reaction mass that will complex with the carbonyl group of the acyloxy reaction site is expected to be an effective catalyst in the method of this invention.

Examples of halide catalysts which are suitable for use in the method of this invention include, but are not limited to, the following: quaternary ammonium halides, such as $Bu_4NBr$, $Bu_4NCl$, $Bu_4NI$; quaternary pyridinium halides, such as $C_5H_5(CH_3)NCl$, $C_5H_5(CH_3)NBr$, $C_5H_5(CH_3)NI$, $C_5H_5(CH_3CH_2)NCl$, $C_5H_5(CH_3CH_2)NBr$, $C_5H_5(CH_3CH_2)NI$ and those disclosed by Mahone, U.S. Pat. No. 4,108,882; quaternary phosphonium halides, such as $Bu_4PCl$ and $Bu_4PBr$ and metal halides, such as $AlCl_3$.

The amount of the halide catalyst to be used is typically from about 0.1 to 10, preferably 1 to 5 percent by weight based on the weight of the reaction mass.

The cyclotetrasiloxanes provided by the method of this invention have all the uses of cyclotetrasiloxanes that are prepared by methods of the art. They can be used, per se, where siloxane fluids are used, and they can also be used to prepare linear and branched homopolymeric and copolymeric polysiloxane fluids, gums and resins. In many cases this invention provides a preferred method for preparing cyclotetrasiloxanes, such as $\{(CH_3)(CH_2=CH)SiO\}_4$, which undesirably undergoes some vinyl radical cleavage, vinyl radical polymerization and a vinyl radical addition of HCl when it is prepared by hydrolyzing the methylvinyldichlorosilane; and $\{(CH_3)(ClOCCH_2CH(CH_3)CH_2)SiO\}_4$, which cannot be obtained from the hydrolysis of the corresponding dichlorosilane.

The method of this invention also provides valuable aliphatic chlorides and acyl chlorides which would be difficult to synthesize by other routes. Advantageously, the aliphatic chlorides can be used directly to prepare valuable silane intermediates.

If desired, the individual reaction products that are produced by the method of this invention can be recovered by conventional separating methods, such as distillation, crystallization, evaporation, decantation, extraction and chromatography.

The following examples are disclosed to further illustrate, but not to limit, the present invention.

Infrared spectra were obtained with a Beckman Acculab 2 spectrophotometer.

Gas-liquid chromatograms (g.l.c.) were obtained with a Hewlett Packard Model HP 5710A chromatograph, fitted with $10' \times \frac{1}{8}''$ stainless steel columns packed with Chromosorb W-HP 100/120 mesh containing 15% by weight OV 101 as the liquid phase, and coupled with a Hewlett Packard Model HP 3380A integrator.

Percent conversion means g.l.c. area percent based on the entire peak area of the chromatogram. Percent yield means weight percent of product obtained based on weight of starting material that reacted.

EXAMPLE 1

Methylvinyldichlorosilane, 1.4 g. (12 m mols), t-butylacetate, 1.0 g. (8.6 m mols) and tetrabutylammonium bromide. 0.005 g. were placed in a glass ampoule, the ampoule was sealed and the sealed ampoule was placed in a stainless steel safety jacket and heated at 150° C. for 10 hours. The heated ampoule was then cooled to about $-75°$ C., was opened and the contents were analyzed by gas-liquid phase chromatography. An 84% yield of $\{(CH_3)(CH_2=CH)SiO\}_4$ was obtained.

EXAMPLE 2

Example 1 was repeated using 2.27 g. (9 m mols) of diphenyldichlorosilane, 1.0 g. (8.6 m mols) of t-butylacetate and 0.07 g. of tetrabutylammonium bromide, except that the reaction mass was heated at 200° C. for 3 hours. A 48% conversion to t-butyl chloride and a 15% conversion to $CH_3COCl$ was obtained.

EXAMPLES 3 TO 7

Dimethyldichlorosilane was converted to $\{(CH_3)_2SiO\}_4$ in various yields according to the procedure of Example 1 using no catalyst or one of several catalysts and several heating conditions. These Examples and their results are summarized in Table I. When Example 7 was repeated, except the temperature was 300° C. and a 4/1 molar ratio of ethylacetate/dimethyldichlorosilane was used, entirely different reaction products were obtained.

TABLE I

| | Reaction Mass | | | Heating | | Results, %[1] | | |
|---|---|---|---|---|---|---|---|---|
| Ex. No. | Compound | Grams | m Mol | °C. | Hrs. | Product | Yield | Conv. |
| 3. | $Me_2SyCl_2$ | 2.6 | 20 | 200 | 8 | [2]$D_3$ | — | trace |
| | $(MeCO)_2O$ | 2.0 | 19 | | | $D_4$ | — | 35 |
| | $Bu_4NBr$ | 0.2 | | | | | | |
| 4. | $Me_2SiCl_2$ | 1.5 | 11.6 | 200 | 10 | [3]$D_4$ | 79 | — |
| | $PhCO_2Me$ | 1.1 | 8.1 | | | MeCl | — | 23 |
| | $Bu_4NBr$ | 0.01 | | | | PhCOCl | — | 4 |
| 5. | $Me_2SiCl_2$ | 2.2 | 17 | 200 | 2 | $D_4$ | — | 8 |
| | $MeCO_2Et$ | 1.5 | 17 | | | EtCl | — | 8 |
| | $AlCl_3$ | 0.02 | | | | MeCOCl | — | 8 |

TABLE I-continued

| Ex. No. | Reaction Mass Compound | Grams | m Mol | Heating °C. | Hrs. | Results, %[1] Product | Yield | Conv. |
|---|---|---|---|---|---|---|---|---|
| 6. | Me$_2$SiCl$_2$ | 1.0 | 7.7 | 220 | 46 | D$_4$ | 86 | — |
|  | MeCO$_2$Me | 1.0 | 13.5 |  |  |  |  |  |
|  | Bu$_4$NBr | 0.01 |  |  |  |  |  |  |
| 7. | Me$_2$SiCl$_2$ | 1.2 | 9.3 | 210 | 18 | [4]D$_4$ | 92 | 5 |
|  | MeCO$_2$Et | 0.8 | 9.1 |  |  | EtCl | — | 5 |
|  | No Cat. | — |  |  |  | MeCOCl | — | 5 |

[1]D$_3$ denotes (Me$_2$SiO)$_3$; D$_4$ denotes (Me$_2$SiO)$_4$
[2]At 180° C. (atm. press. reflux) for 2 days only (CH$_3$)$_2$ClSiO$_2$CCH$_3$ was recovered.
[3]At 150° C. for 5 hours only (CH$_3$)$_2$ClSiO$_2$CPh and CH$_3$Cl were formed.
[4]At 200° C. for 15 hours no D$_4$ was formed.

EXAMPLE 8

Methyl 2-dichloromethylsilylisobutyrate (Cl$_2$CH$_3$SiCH$_2$CH(CH$_3$)CO$_2$CH$_3$) was prepared according to Speier et al. *J. Am. Chem. Soc.*, 79, 974 (1957) using 500 g. of methyl methacrylate, 598 g. of methyldichlorosilane and 1 ml. of a 50% solution of H$_2$PtCl$_6$ in isopropanol. The product was isolated in 99.7% purity by vacuum distillation at 60°-65° C/1 Torr.

One gram of Cl$_2$CH$_3$SiCH$_2$CH(CH$_3$)CO$_2$CH$_3$ was sealed in a glass ampoule and heated for 18 hours at 250° C. The heated ampoule was cooled, was opened and the vapor phase and the liquid phase were analyzed. The vapor phase consisted solely of CH$_3$Cl. The liquid phase consisted solely of {(CH$_3$)(CH$_2$CH(CH$_3$)COCl)SiO}$_4$, the infrared spectrum of which in CCl$_4$ showed an absorption at 1730 cm$^{-1}$ for the —COCl radical and at 1100 cm$^{-1}$ for the Si—O—Si linkage and no absorption at 2840 cm$^{-1}$ for the —CO$_2$Me radical. Molecular weight by vapor phase osmometry was 625 and 700; Calculated 658.

When this reaction was repeated at 230° C. for 2 hours or at 200° C. for 20 hours, no reaction occurred. Heating at 290° C. for 3.5 hours produced numerous unidentified products.

When the 200° C. reaction was repeated except that 1.2 g. (9.0 millimols) of (CH$_3$)$_2$SiCl$_2$ was mixed with 1.0 g. (4.5 millimols) of the Cl$_2$CH$_3$SiCH$_2$CH(CH$_3$)CO$_2$CH$_3$ several unidentified products were detected by g.l.c.

The liquid-phase product from the above 250° C. reaction was hydrolyzed with aqueous HCl to form {(CH$_3$)(HO$_2$CCH(CH$_3$)CH$_2$)SiO}$_4$, the infrared spectrum of which, in CCl$_4$, had absorption at 3000 cm$^{-1}$ and at 1740 cm$^{-1}$ for the COOH radical and at 1100 cm$^{-1}$ for the Si—O—Si linkage.

EXAMPLE 9

A reaction mass was prepared by sealing a mixture of 1 g. of Cl$_2$CH$_3$SiCH$_2$CH(CH$_3$)CO$_2$CH$_3$ and 0.01 g. of methylpyridinium chloride in a glass ampoule and heating the sealed ampoule at 250° C. for 6 hours. The starting silane was converted completely to the cyclotetrasiloxane {(CH$_3$)(CH$_2$CH(CH$_3$)COCl)SiO}$_4$.

EXAMPLE 10

A reaction mass of 1 g. of Cl$_2$CH$_3$SiCH$_2$CH(CH$_3$)CO$_2$CH$_3$ and 0.03 g. of methylpyridinium chloride was heated at 150° C. for 18 hours in a vented flask. A 100% conversion to the cyclotetrasiloxane shown in Example 9 was obtained.

EXAMPLE 11

A mixture of 207.9 g. of Cl$_2$CH$_3$SiCH$_2$CH(CH$_3$)CO$_2$CH$_3$ and 6.0 g. of tetra-n-butylammonium bromide was heated at 145° C. for 60 minutes in a vented flask swept with a nitrogen purge. Approximately 150 g. (95% yield) of{(CH$_3$)(CH$_2$CH(CH$_3$)COCl)SiO}$_4$ was obtained.

EXAMPLE 12

A mixture of 6.2 g. of Cl$_2$CH$_3$SiCH$_2$CH(CH$_3$)CO$_2$CH$_3$ and 0.2 g. of ethylpyridinium bromide was heated in a vented flask swept with a nitrogen purge. Evolution of CH$_3$Cl began at 175° C.±5° C. After 2.5 hours at 95% yield of {(CH$_3$)(CH$_2$CH(CH$_3$)COCl)SiO}$_4$ was obtained.

EXAMPLE 13

A mixture of 2.0 g. of Cl$_2$CH$_3$SiCH$_2$CH(CH$_3$)CO$_2$CH$_3$ and 0.04 g. of tetrabutylammonium iodide was heated in a vented flask. An intense red-orange color developed at 130° C. and gradually faded as CH$_3$Cl was evolved. The reaction was complete within 30 minutes and the product was {(CH$_3$)(CH$_2$CH(CH$_3$)COCl)SiO}$_4$.

EXAMPLE 14

A mixture of 1.6 g. of Cl$_2$CH$_3$SiCH$_2$CH(CH$_3$)CO$_2$CH$_3$ and 0.03 g. of tetrabutylphosphonium bromide was heated at 100° C. for 2 hours in a vented flask. Evaluation of CH$_3$Cl was rapid, initially, and {(CH$_3$)(CH$_2$CH(CH$_3$)COCl)SiO}$_4$ was the product, according to g.l.c. analysis.

EXAMPLE 15

Example 1 was repeated using 1.0 g. (6.7 millimols) of CH$_3$SiCl$_3$, 0.49 g. (6.7 millimols) of CH$_3$CO$_2$CH$_3$ and 0.03 g. of Bu$_4$NBr. After being heated for 20 hours at 250° C. this reaction mass provided a 94% yield of {(Cl)(CH$_3$)SiO}$_4$. No reaction occurred at 200° C. for 20 hours.

EXAMPLE 16

Example 1 was repeated using 1.0 g. (5.9 millimols) of SiCl$_4$, 0.45 g. (6 millimols) of CH$_3$CO$_2$CH$_3$ and no catalyst. After being heated at 250° C. for 6 hours this reaction mass provided a 6% conversion of {(Cl)$_2$SiO}$_4$.

EXAMPLES 17 AND 18

Acetoxypropyltrichlorosilane (Cl$_3$SiCH$_2$CH$_2$CH$_2$O$_2$CCH$_3$), 2.5 g., and AlCl$_3$, 0.03 g., were heated in a sealed ampoule at 140° C. for 16 hours. A 100% conversion to CH$_3$COCl and a higher boiling oily product was obtained. A 72% conversion to CH$_3$COCl was obtained when the reaction was repeated in the absence of a catalyst at 250° C. for 20 hours.

That which is claimed is:
1. A method for preparing a cyclotetrasiloxane and an aliphatic chloride and/or an acyl chloride, said method comprising heating a reaction mass selected from the group consisting of (A) a silylhydrocarbonoxy acylate having the formula $$R^1_a Cl_{(3-a)}SiQO_2CR^2,$$

(B) a hydrocarbonoxy silylacylate having the formula $$R^1_a Cl_{(3-a)}SiQCO_2R^2,$$

and (C) a mixture of equimolar amounts of
(i) a silane having the formula $R^1_b SiCl_{(4-b)}$ and
(ii) an acyloxy compound selected from the group consisting of hydrocarbon carboxylic esters and hydrocarbon carboxylic anhydrides, wherein, at each occurrence,
a denotes a number having a value of 0 or 1;
b denotes a number having a value of 0, 1 or 2;
$R^1$ denotes a monovalent substituted or unsubstituted hydrocarbon radical;
$R^2$ denotes a monovalent unsubstituted hydrocarbon radical;
Q denotes a divalent substituted or unsubstituted hydrocarbon radical; any hydrocarbon radical bonded to an oxygen atom of an acyloxy radical being bonded at an aliphatic carbon atom of said any hydrocarbon radical; said heating being sufficient to produce a cyclotetrasiloxane wherein each silicon atom bears two-fewer chlorine atoms than were present on each silicon atom in the reaction mass and at least one reaction product selected from the group consisting of an acyl chloride and an aliphatic chloride; the substituents of said substituted hydrocarbon radicals being non-reactive during said heating.

2. A method according to claim 1 wherein the reaction mass consists essentially of a silylhydrocarbonoxy acylate having the formula $R^1_a Cl_{(3-a)}SiC_nH_{2n}O_2CR^2$ wherein n denotes a number having a value of from 2 to 4, said reaction mass being heated sufficiently to form an aliphatic chloride-substituted cyclotetrasiloxane reaction product having the formula

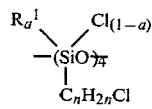

and an acyl chloride reaction product having the formula $R^2COCl$.

3. A method according to claim 2 wherein a has a value of 1 and $R^1$ denotes a radical selected from the group consisting of hydrocarbon radicals having from 1 to 6 carbon atoms, and halogenated derivatives thereof, and $R^2$ denotes a lower alkyl radical.

4. A method according to claim 3 wherein $R^1$ denotes the methyl radical.

5. A method according to claim 1 wherein the reaction mass consists essentially of a hydrocarbonoxy silylacylate having the formula $R^1_a Cl_{(3-a)}SiC_nH_{2n}CO_2R^2$ wherein n denotes a number having a value of from 2 to 4, said reaction mass being heated sufficiently to form an acid chloride-substituted cyclotetrasiloxane reaction product having the formula

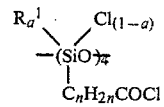

and an aliphatic chloride reaction product having the formula $R^2Cl$.

6. A method according to claim 5 wherein a has a value of 1 and $R^1$ denotes a radical selected from the group consisting of hydrocarbon radicals having from 1 to 6 carbon atoms and halogenated derivatives thereof and $R^2$ denotes a lower alkyl radical.

7. A method according to claim 6 wherein $R^1$ denotes the methyl radical.

8. A method according to claim 1 wherein the reaction mass consists essentially of an equimolar mixture of
(i) a silane having the formula $R^1_b SiCl_{(4-b)}$ wherein $R^1$ denotes a monovalent substituted or unsubstituted hydrocarbon radical and b has a value of 0, 1 or 2 and
(ii) a hydrocarbon carboxylic ester having the formula $R^2CO_2R^2$, said reaction mass being heated sufficiently to form a cyclotetrasiloxane having the formula

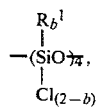

an acyl chloride having the formula $R^2COCl$ and an aliphatic chloride having the formula $R^2Cl$.

9. A method according to claim 8 wherein b has a value of 2 and each $R^1$ denotes, independently, a radical selected from the group consisting of hydrocarbon radicals having from 1 to 6 carbon atoms and halogenated derivatives thereof and $R^2$ denotes, independently, a lower alkyl radical.

10. A method according to claim 9 wherein each $R^1$ denotes the methyl radical.

11. A method according to claim 9 wherein one $R^1$ denotes the methyl radical and the other $R^1$ denotes the vinyl radical.

12. A method according to claim 1, 2, 3, 4, 5, 6, 7, 8, 9, 10 or 11 wherein the reaction mass being heated comprises an amount of a halide salt wherein the halide portion is selected from chloride, bromide and iodide cations, said halide salt being present in a sufficient amount and being sufficiently soluble in the reaction mass during said heating, to provide a catalytically effective amount of the halide salt dissolved in the reaction mass.

13. A method according to claim 12 wherein the halide salt is selected from quaternary ammonium halide salts, quaternary phosphonium halide salts and quaternary pyridinium halide salts.

* * * * *